(12) United States Patent
Janik

(10) Patent No.: US 7,006,596 B1
(45) Date of Patent: Feb. 28, 2006

(54) LIGHT ELEMENT MEASUREMENT

(75) Inventor: Gary R. Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 29 days.

(21) Appl. No.: 10/434,861

(22) Filed: May 9, 2003

(51) Int. Cl.
*G01N 23/223* (2006.01)

(52) U.S. Cl. .................... 378/45; 378/84; 378/145; 250/310

(58) Field of Classification Search ............. 250/310, 250/370.06, 505.1, 397; 378/147, 46, 98.6, 378/98
See application file for complete search history.

(56) References Cited

U.S. PATENT DOCUMENTS

| | | | | |
|---|---|---|---|---|
| 5,175,755 A | * | 12/1992 | Kumakhov | 378/34 |
| 5,192,869 A | * | 3/1993 | Kumakhov | 250/505.1 |
| 5,280,513 A | * | 1/1994 | Meltzer | 378/90 |
| 5,333,166 A | * | 7/1994 | Seligson et al. | 378/34 |
| 5,497,008 A | * | 3/1996 | Kumakhov | 250/505.1 |
| 5,682,415 A | | 10/1997 | O'Harar | 378/147 |
| 5,745,547 A | * | 4/1998 | Xiao | 378/145 |
| 5,810,469 A | * | 9/1998 | Weinreich | 362/298 |
| 6,108,398 A | * | 8/2000 | Mazor et al. | 378/45 |
| 6,442,231 B1 | | 8/2002 | O'Hara | 378/45 |
| 6,453,002 B1 | * | 9/2002 | Mazor et al. | 378/49 |
| 2003/0002620 A1 | * | 1/2003 | Mazor et al. | 378/49 |
| 2004/0131146 A1 | * | 7/2004 | Chen et al. | 378/41 |

OTHER PUBLICATIONS

U.S. Appl. No. 09/695,726, Shing Lee.

* cited by examiner

*Primary Examiner*—Nikita Wells
*Assistant Examiner*—Johnnie L Smith, II
(74) *Attorney, Agent, or Firm*—Luedeka, Neely & Graham, P.C.

(57) ABSTRACT

A spectrometer for detecting and quantifying elements in a sample. An exciter ionizes atoms in the sample, and the atoms thereby produce characteristic x-rays. A detector receives the x-rays and produces signals based on the x-rays. A filter system selectively blocks the x-rays from attaining the detector. The selective blocking of the x-rays is accomplished based on an energy of the x-rays. An analyzer receives the signals from the detector and detects and quantifies the elements in the sample based at least in part on the signals. In this manner, detector receives the light element x-rays, and the medium and heavy element x-rays are filtered out to avoid overwhelming the detector. This invention combines the large solid angle, high efficiency, and ability to measure the continuous background spectrum of the energy dispersive x-ray detector with the selectivity of the wavelength dispersive x-ray detector. It thus enables faster and more accurate measurement of light elements in thin films. This invention enhances the light element performance of a system by enabling higher throughput, lower e-beam and x-ray dose to the sample, and improved accuracy from the capability to measure the background radiation.

16 Claims, 1 Drawing Sheet

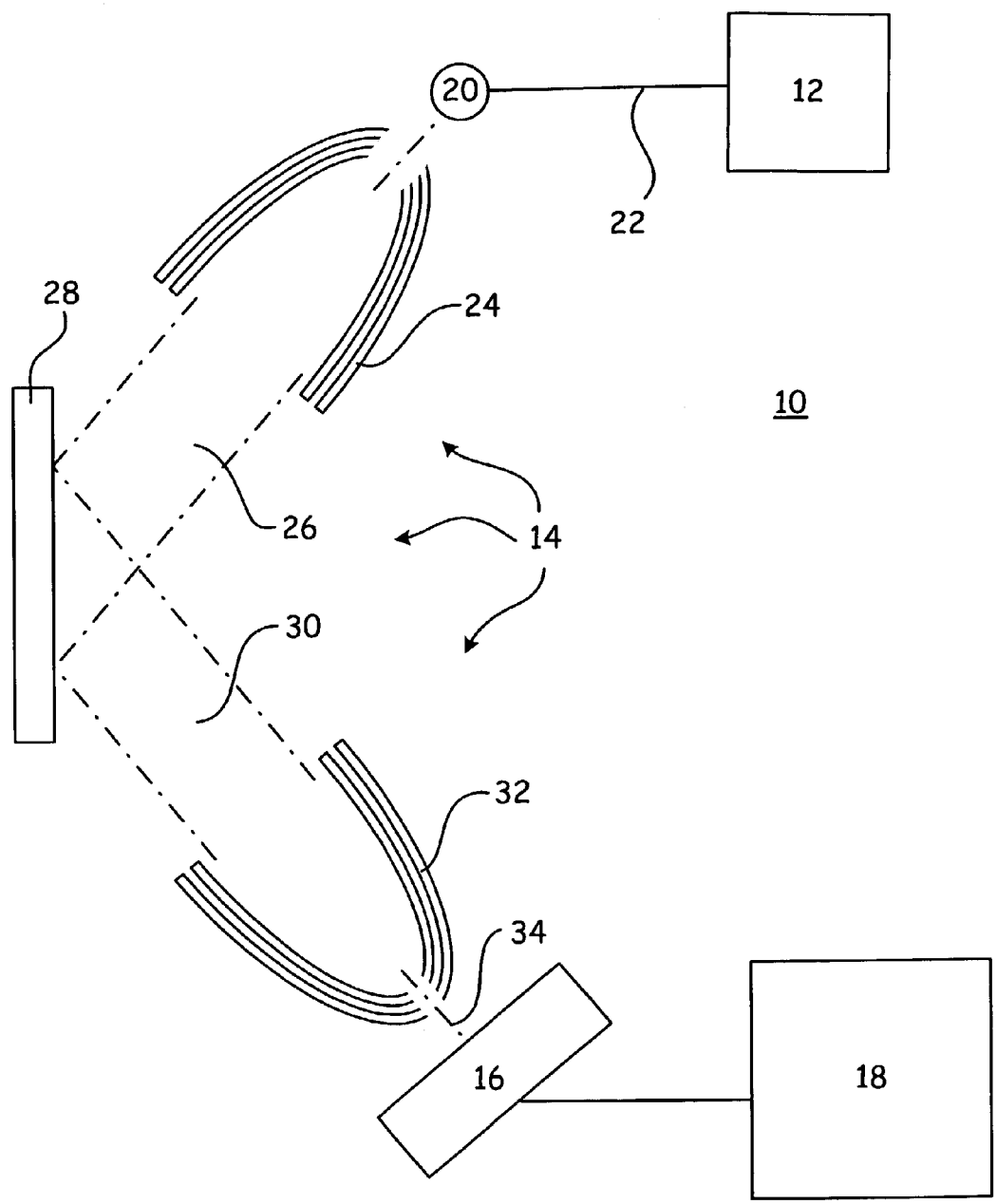

LIGHT ELEMENT MEASUREMENT

FIELD

This invention relates to the field of instrumentation for materials analysis. More particularly, this invention relates to measuring light molecular weight element concentrations in thin films using electron microprobe or x-ray fluorescence techniques.

BACKGROUND

Materials analysis is an important technology for many industries, including the integrated circuit fabrication industry, where the ability to confirm the stoichiometry of the various layers that are formed during the fabrication of an integrated circuit is essential. Analysis techniques generally distinguish elements based upon unique properties of the elements, such as molecular weight. For a variety of reasons, relatively lighter molecular weight elements, otherwise referred to herein as light elements, tend to be somewhat more difficult to detect. As used herein, light elements have a molecular weight of no more than about twenty-one atomic mass units.

One method of measuring relatively light molecular weight elements in thin films is to use a wavelength dispersive x-ray detector tuned to the characteristic x-ray line of the desired light element. Another method is to use an energy dispersive x-ray detector to detect the entire spectrum of x-rays including medium and heavy elements, as well as the continuous bremsstrahlung radiation.

The wavelength dispersive x-ray method suffers from a limited solid angle that can be collected due to the geometry necessary to satisfy the Bragg condition for the reflection of x-rays. Another disadvantage of the wavelength dispersive x-ray method is that the Bragg reflector generally has a low efficiency, usually less than about ten percent. A third disadvantage of the wavelength dispersive x-ray method is the inability to measure the continuous x-ray background at neighboring wavelengths. It is necessary to add a second wavelength dispersive x-ray detector to measure the background at a single neighboring wavelength, which does not always yield adequate information.

Energy dispersive x-ray analysis characterizes materials by exciting a sample with ionizing radiation. An energy-dispersive x-ray analyzer is a common accessory for a scanning electron microscope. The electron beam in the scanning electron microscope typically has an energy of between about five thousand and about twenty thousand electron volts, and provides the ionizing radiation. The binding energy in an atom ranges from a few electron volts up to many thousand electron volts. Atomic electrons are dislodged as the incident electrons from the scanning electron microscope beam pass through the sample, thus ionizing atoms of the sample.

After an atomic electron is ejected from the sample, another electron, such as from a nearby atom, neutralizes the ionized atom. This neutralization produces an x-ray with an energy level that is characteristic of the sample atom. Another mechanism, known as bremsstrahlung, also produces x-rays. In this case an electron from the beam is significantly deflected by the strong electric field of an atom's nucleus. As the electron curves around the nucleus, it emits an x-ray. These x-rays can be emitted over a wide, continuous energy range and are not characteristic of the atom which produced them. By using x-ray detection equipment to count the number of x-ray photons emitted at a given energy level, the energy dispersive x-ray system is able to characterize and quantify the elemental composition of the sample.

The energy dispersive x-ray method overcomes the problems of wavelength dispersive x-ray, but suffers from its sensitivity to all the x-rays, including bremsstrahlung from the light element atoms and both bremsstrahlung and characteristic x-rays from the medium and heavy elements. Generally the x-rays from medium and heavy x-rays are much more intense than those from the light elements, and can overwhelm the energy dispersive x-ray detector with too high a count rate.

What is needed, therefore, is a system for light element material analysis that at least reduces some of the problems with the currently used techniques.

SUMMARY

The above and other needs are met by a spectrometer for detecting and quantifying elements in a sample. An exciter ionizes atoms in the sample, and the atoms thereby produce x-rays. A detector receives the x-rays and produces signals based on the x-rays. A filter system selectively blocks some of the x-rays from attaining the detector. The selective blocking of the x-rays is accomplished based on an energy of the x-rays. An analyzer receives the signals from the detector and detects and quantifies the elements in the sample based at least in part on the signals.

In this manner, the detector receives the light element x-rays, and most of the medium and heavy element x-rays are filtered out to avoid overwhelming the detector. This invention combines the large solid angle, high efficiency, and ability to measure the continuous background spectrum of the energy dispersive x-ray detector with the selectivity of the wavelength dispersive x-ray detector. It thus enables faster and more accurate measurement of light elements in thin films. This invention enhances the light element performance of a system by enabling higher throughput, lower e-beam and x-ray dose to the sample, and improved accuracy from the capability to measure the background radiation.

In various preferred embodiments, the filter system includes a collimator that collects the x-rays emitted from the sample. The collimator absorbs, or alternately does not deflect, x-rays having an energy greater than a first desired energy, and directs x-rays having an energy less than the first desired energy along a collimated beam. A reflector receives the collimated beam from the collimator at an angle of incidence that is below a critical angle for energies of the x-rays in the collimated beam that are below a desired cutoff energy. Thus, x-rays in the collimated beam with an energy less than the desired cutoff energy are reflected, and x-rays in the collimated beam with an energy greater than the desired cutoff energy are either absorbed or transmitted through the reflector.

In a most preferred embodiment, the first desired energy is about four thousand electron volts, and the desired cutoff energy is about five hundred electron volts. Most preferably, the collimator comprises a series of concentric parabolic collimators having smooth metallic surfaces with angles of reflection that are arranged such that the collimator absorbs or does not deflect x-rays having an energy greater than the first desired energy, and directs x-rays having an energy of less than the first desired energy along the collimated beam. Preferably, a second collimator receives the collimated beam from the reflector and refocuses the collimated beam onto the detector. The first desired energy and the desired cutoff energy are preferably adjustable by means of changes to the geometry and materials of the collimator and reflector, respectively.

According to another aspect of the invention, there is described a scanning electron microscope of the type having an electron beam that ionizes atoms in a sample, where the atoms thereby produce x-rays. A detector receives the x-rays and produces signals based on the x-rays. A filter system selectively blocks the x-rays from attaining the detector, where the selective blocking of the x-rays is accomplished based on an energy of the x-rays. An analyzer receives the signals from the detector and detects and quantifies elements in the sample based at least in part on the signals.

According to yet another aspect of the invention, there is described an energy dispersive x-ray spectrometer having a filter system adapted to selectively block x-rays ejected from a sample. The selective blocking of the x-rays is accomplished based on an energy of the x-rays.

BRIEF DESCRIPTION OF THE DRAWINGS

Further advantages of the invention are apparent by reference to the detailed description when considered in conjunction with the figure, which is not to scale so as to more clearly show the details, and which is a functional block diagram of a system according to the present invention.

DETAILED DESCRIPTION

With reference now to the figure, there is depicted a functional block diagram of a system 10 according to the present invention. The system 10 may be scanning electron microscope in which the elements as described are incorporated, or a standalone spectrometer, such as an energy dispersive x-ray fluorescent spectrometer, in which various elements have been added. The major parts of the system 10 are an exciter 12, filter system 14, detector 16, and analyzer 18. The filter system 14 preferably includes at least a collimator 24 and reflector 28, and optionally includes a second collimator 32. One function of the system 10 is to detect and quantify elements, and more especially light elements, in a sample 20.

An electron beam or x-ray beam 22 stimulates the emission of x-rays from a small spot on a sample 20 that contains one or more light elements, such as nitrogen, carbon, and oxygen. X-rays emitted from the sample 20 are collected by a collimator 24, which is preferably a parabolic collimator, and most preferably a series of concentric parabolic collimators that are disposed around the sample 20 as shown in the figure. The collimator 24 reflects the x-rays diverging from the emission spot into a collimated beam 26. The collimator 24 preferably has smooth metallic surfaces. The angles of reflection of the surfaces are preferably arranged such that only x-rays with energies less than a first desired energy, preferably about four thousand electron volts, are completely reflected outside of the collimator 24 and along the collimated beam 26. Higher energy x-rays are preferably absorbed by the collimator 24.

Without being bound by theory, it is understood that typically only atoms with an atomic number of less than about twenty-one have K shell x-rays with energies less than about four thousand electron volts, so the collimator 24 is preferably adapted to filter out K x-rays from elements that are heavier than calcium. Medium and heavy atoms also emit L shell x-rays that are preferably filtered. In particular, copper emits L x-rays with an energy of about nine hundred and thirty electron volts. In addition, heavy elements emit low energy M shell x-rays. As an example, tantalum emits M x-rays at eighteen hundred electron volts.

The L and heavy element M x-rays are preferably filtered by reflecting the collimated beam 26 from a reflector 28, which is most preferably a flat metal surface. The reflector 28 is configured with an angle of incidence to the collimated beam 26 that is below the critical angle for x-rays in the collimated beam 26 that have an energy that is below a desired cut off energy, such as about five hundred electron volts. In this manner, x-rays in the collimated beam 26 that have an energy that is less than the desired cutoff energy are almost completely reflected by the reflector 28. However, those x-rays in the collimated beam 26 that have an energy that is above the desired cutoff energy, or in other words have a critical angle that is less than the angle of incidence of the collimated beam 26 against the reflector 28, are absorbed by or are transmitted through the reflector 28.

Thus, higher energy x-rays are absorbed by the reflector 28, and lower energy x-rays are reflected by the reflector 28. Thus, the reflector 28 helps to further filter the x-rays emitted by the sample 20. The x-rays 30 reflected from the reflector 28 correspond mostly to characteristic x-rays emitted from light elements. Other x-rays that may be reflected are: low-energy bremsstrahlung from all elements, medium element M x-rays, and heavy element N x-rays. These other x-rays are generally very weak. The reflected x-rays 30 are detected by a detector 16, which produces signals based upon the x-rays, such as the energy with which they are received, and the amount of x-rays that are received at a given energy. Thus, the detector 16 detects characteristic x-rays that indicate both the materials of which the sample 20 is comprised, and the relative amounts of those materials. In a most preferred embodiment, the detector 16 is one such as is found in a standard energy dispersive x-ray system.

The signals produced by the detector 16 are preferably sent to an analyzer 18, which determines the materials in the sample 20, and the relative amounts of such materials, such as by comparing the signals that are received to a database of information that correlates such signals to known elements. The analyzer 18 is preferably one such as is found in a standard energy dispersive x-ray system.

In a preferred embodiment, the collimated beam 30 reflected from the reflector 28 is refocused with a second collimator 32 as depicted in the figure. This configuration allows a smaller detector 16 to be used, which tends to reduce the cost and improve the energy resolution of the system 10. The material and angle of the reflector 28 is preferably variable, to selectively adjust the desired cutoff energy. The system 10 can optionally include other detectors, such as prior art energy dispersive x-ray detectors and wavelength dispersive x-ray detectors, to simultaneously measure medium and heavy elements that may be present in the sample 20.

As a specific example, the system 10 can be used to measure a copper/TaN barrier seed film on a semiconductor wafer 20. The copper is twelve hundred angstroms thick on top of a one hundred angstrom TaN barrier film. Two wavelength dispersive x-ray detectors tuned to the copper K (eight thousand electron volts) and tantalum L (eighty-four hundred electron volts) x-rays are used to measure the quantity of copper and tantalum. A parabolic collimator 24 followed by a cutoff mirror reflector 28 are used with an energy dispersive x-ray detector 16 to measure the nitrogen and its neighboring background. The cutoff of the mirror 28 is set at four hundred and fifty electron volts to filter out the nine hundred and thirty electron volt copper L x-rays, as well as the eighteen hundred electron volt silicon K x-rays and the eighteen hundred electron volt tantalum M x-rays.

Thus, in the system 10 as described herein, the detector 16 receives the light element x-rays, and the medium and heavy element x-rays are filtered out to avoid overwhelming the detector 16. Therefore, this invention enables faster and more accurate measurement of light elements in thin films, and enhances the light element performance of a system by enabling higher throughput, lower e-beam and x-ray dose to the sample 20, and improved accuracy from the capability to measure the background radiation.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A spectrometer for detecting and quantifying elements in a sample, the spectrometer comprising:
    an exciter adapted to ionize atoms in the sample, the atoms thereby producing x-rays,
    a detector adapted to receive the x-rays and produce signals based on the x-rays,
    a filter system adapted to selectively block the x-rays from attaining the detector,
        where the selective blocking of the x-rays is accomplished based on an energy of the x-rays, the filter system including,
            a parabolic collimator having a smooth metallic surface disposed around the sample and adapted to collect the x-rays emitted from the sample, where the collimator absorbs x-rays having an energy greater than a first desired energy, and directs x-rays having an energy less than the first desired energy along a collimated beam, and
            a reflector adapted to receive the collimated beam from the collimator at an angle of incidence that is below a critical angle for energies of the x-rays in the collimated beam that are below a desired cutoff energy of about five hundred electron volts, thereby reflecting x-rays in the collimated beam with an energy less than the desired cutoff energy and absorbing x-rays in the collimated beam with an energy greater than the desired cutoff energy, and
    an analyzer adapted to receive the signals from the detector and to detect and quantify the elements in the sample based at least in part on the signals.

2. The spectrometer of claim 1, wherein the first desired energy is about four thousand electron volts.

3. The spectrometer of claim 1, wherein the desired cutoff energy is about five hundred electron volts.

4. The spectrometer of claim 1, wherein the collimator comprises a series of concentric parabolic collimators disposed around the sample and directed toward the reflector.

5. The spectrometer of claim 1, wherein the collimator comprises a series of concentric parabolic collimators having smooth metallic surfaces disposed around the sample and directed toward the reflector.

6. The spectrometer of claim 1, wherein the collimator comprises a series of concentric parabolic collimators having smooth metallic surfaces with angles of reflection that are arranged such that the collimator absorbs x-rays having an energy greater than the first desired energy, and directs x-rays having an energy of less than the first desired energy along the collimated beam.

7. The spectrometer of claim 1, further comprising a second collimator adapted to receive the collimated beam from the reflector and refocus the collimated beam onto the detector.

8. The spectrometer of claim 1, wherein the first desired energy and the desired cutoff energy are adjustable.

9. In a scanning electron microscope of the type having an electron beam that ionizes atoms in a sample, the atoms thereby producing x-rays, the improvement comprising:
    a detector adapted to receive the x-rays and produce signals based on the x-rays,
    a filter system adapted to selectively block the x-rays from attaining the detector, where the selective blocking of the x-rays is accomplished based on an energy of the x-rays, the filter system including,
        a parabolic collimator having a smooth metallic surface disposed around the sample and adapted to collect the x-rays emitted from the sample, where the collimator absorbs x-rays having an energy greater than a first desired energy, and directs x-rays having an energy less than the first desired energy along a collimated beam, and
        a reflector adapted to receive the collimated beam from the collimator at an angle of incidence that is below a critical angle for energies of the x-rays in the collimated beam that are below a desired cutoff energy of about five hundred electron volts, thereby reflecting x-rays in the collimated beam with an energy less than the desired cutoff energy and absorbing x-rays in the collimated beam with an energy greater than the desired cutoff energy, and
    an analyzer adapted to receive the signals from the detector and to detect and quantify elements in the sample based at least in part on the signals.

10. The scanning electron microscope of claim 9, wherein the first desired energy is about four thousand electron volts.

11. The scanning electron microscope of claim 9, wherein the desired cutoff energy is about five hundred electron volts.

12. The scanning electron microscope of claim 9, wherein the collimator comprises a series of concentric parabolic collimators having smooth metallic surfaces with angles of reflection that are arranged such that the collimator absorbs x-rays having an energy greater than the first desired energy, and directs x-rays having an energy of less than the first desired energy along the collimated beam.

13. In an energy dispersive x-ray spectrometer having a detector, the improvement comprising a filter system adapted to selectively block x-rays ejected from a sample from attaining the detector, where the selective blocking of the x-rays is accomplished based on an energy of the x-rays, the filter system including,
    a parabolic collimator having a smooth metallic surface disposed around the sample and adapted to collect the x-rays emitted from the sample, where the collimator absorbs x-rays having an energy greater than a first desired energy, and directs x-rays having an energy less than the first desired energy along a collimated beam, and a reflector adapted to receive the collimated beam from the collimator at an angle of incidence that is below a critical angle for energies of the x-rays in the collimated beam that are below a desired cutoff energy of about five hundred electron volts, thereby reflecting x-rays in the collimated beam with an energy less than the desired cutoff energy and absorbing x-rays in the collimated beam with an energy greater than the desired cutoff energy.

14. The energy dispersive x-ray spectrometer of claim 13, wherein the first desired energy is about four thousand electron volts.

15. The energy dispersive x-ray spectrometer of claim 13, wherein the desired cutoff energy is about five hundred electron volts.

16. The energy dispersive x-ray spectrometer of claim 13, wherein the collimator comprises a series of concentric parabolic collimators having smooth metallic surfaces with angles of reflection that are arranged such that the collimator absorbs x-rays having an energy greater than the first desired energy, and directs x-rays having an energy of less than the first desired energy along the collimated beam.

* * * * *